(12) United States Patent
Venditti (10) Patent No.: US 8,721,988 B2
(45) Date of Patent: May 13, 2014

(54) METHOD FOR DIRECT MEASUREMENT OF ISOTOPES OF EXPIRED GASES

(75) Inventor: Charles P. Venditti, Kensington, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 40 days.

(21) Appl. No.: 13/620,490

(22) Filed: Sep. 14, 2012

(65) Prior Publication Data

US 2013/0009054 A1    Jan. 10, 2013

Related U.S. Application Data

(62) Division of application No. 12/418,795, filed on Apr. 6, 2009, now Pat. No. 8,293,187.

(51) Int. Cl.
*G01N 33/00* (2006.01)

(52) U.S. Cl.
USPC .............................. 422/401; 422/83; 422/500

(58) Field of Classification Search
USPC ............................................ 422/50, 83, 401
See application file for complete search history.

(56) References Cited

U.S. PATENT DOCUMENTS

| | | | |
|---|---|---|---|
| 5,293,875 A * | 3/1994 | Stone | ............................ 600/532 |
| 5,626,151 A | 5/1997 | Linden | |
| 5,975,081 A * | 11/1999 | Hood et al. | .................... 128/845 |
| 7,465,276 B2 | 12/2008 | Assadi-Porter et al. | |
| 8,293,187 B2 * | 10/2012 | Venditti et al. | ................. 422/401 |
| 2007/0023641 A1 * | 2/2007 | Weitz | ............................. 250/288 |
| 2008/0202213 A1 * | 8/2008 | Villers et al. | ................... 73/49.3 |

OTHER PUBLICATIONS

Blaak et al., "Impaired Oxidation of Plasma-Derived Fatty Acids in Type 2 Diabetic Subjects During Moderate-Intensity Exercise", Diabetes, vol. 49, pp. 2102-2107 (2000).
Goodpaster et al., "Effect of Obesity on Substrate Utilization During Exercise", Obesity Research, vol. 10 (7), pp. 575-584 (2002).
Matsumoto et al., "Validation of 13C-Acetic Acid Breath Test by Measuring Effects of Loperamide, Morphine, Mosapride, and Itopride on Gastric Emptying in Mice," Biol. Pharm. Bull. (2008), 31(10)1917-1922.
Mohn et al., "Feeding Frequency and Type of Isotope Tracer do not Affect Direct Estimates of Lysine Oxidation in Growing Pigs", American Society for Nutritional Studies, pp. 3503-3508 (2003).

(Continued)

*Primary Examiner* — Sam P Siefke
(74) *Attorney, Agent, or Firm* — Edwards Wildman Palmer LLP; Peter F. Corless; Lisa Swiszcz (57) ABSTRACT

The invention provides a device including a chamber wherein the chamber including a rigid enclosure; a rigid lid for the enclosure; a gasket between the lid and the enclosure to allow for an airtight seal between the enclosure and the gasket upon closure of a latch connecting the enclosure and the lid; a port for airtight attachment of a syringe, and a port for airtight insertion of a gas sensor. The device can further include a gas sensor and one or more syringes for attachment to the device by a three-way stopcocks. The device is appropriately sized for use with the subject of interest. The invention also provides methods for use of the device.

6 Claims, 8 Drawing Sheets

(56) References Cited

OTHER PUBLICATIONS

Symonds et al., "Assessment of Gastric Emptying in the Mouse Using the [13C]-Octanoic Acid Breath Test," Clin. and Exper. Pharm. and Physiology (2000), 27:671-675.

Tabiri et al, "Development of the Indicator Amino Acid Oxidation Technique in Chickens: Calibration of Oxidation System and Determination of Bicarbonate Retention Factor", Poultry Science Association, Inc., pp. 1020-1025 (2002).

Uchida et al., "13C-Acetic Acid is More Sensitive Than 13C-Octanoic Acid for Evaluating Gastric Emptying of Liquid Enteral Nutrient Formula by Breath Test in Conscious Rats," Biol. Pharm. Bull. (2007), 30(3):487-489.

van Loon et al., The use of the [1,2-13C]acetate Recovery Factor in Metabolic Research, Eur. J. App. Physiol., vol. 89, pp. 377-383 (2003).

\* cited by examiner

METHOD FOR DIRECT MEASUREMENT OF ISOTOPES OF EXPIRED GASES

CROSS-REFERENCED TO RELATED APPLICATIONS

This application is a divisional of U.S. patent application Ser. No. 12/418,795, Filing Date, Apr. 6, 2009, the disclosure of each of which is incorporated herein by reference in its entirety for all purposes.

STATEMENT OF RIGHTS TO INVENTIONS MADE UNDER FEDERALLY SPONSORED RESEARCH

This work was supported in part by the National Institutes of Health. The government has certain rights in the invention.

BACKGROUND

The use of isotope tracers to study metabolism has long been known. Samples of body fluids or exhaled gas are typically collected from the subject at discrete intervals at times after administration of isotopically labeled (e.g., $^2$H, $^{13}$C, $^{15}$N, $^{18}$O) substrate for metabolism by the subject (e.g., amino acids, sugars, fats). Exhaled gases can be collected using an open circuit device in which the subject inhales air through a mouthpiece from a defined source, and the exhaled air is collected. A similar open circuit method can be used in an oxygen tent like setting in which air is delivered in a controlled manner to the chamber, but because the circuit is open, volumes and concentrations of inhaled and exhaled gases are harder to precisely measure. The amount of isotope present in the sample can be determined using known methods such as Isotope Ratio Mass Spectroscopy (IRMS). The sample is processed before entering the mass spectrometer so that only a single chemical species enters at a given time. Generally, samples are combusted or pyrolyzed and the desired species (usually hydrogen gas $H_2$, nitrogen ($N_2$), carbon dioxide ($CO_2$), or sulfur dioxide) is purified by means of traps, filters, catalysts and/or chromatography.

The two most common types of IRMS instruments are continuous flow and dual inlet. In dual inlet IRMS, purified gas obtained from a sample is alternated rapidly with a standard gas (of known isotopic composition) by means of a system of valves, so that a number of comparison measurements are made of both gases. In continuous flow IRMS, sample preparation occurs immediately before introduction to the IRMS, and the purified gas produced from the sample is measured just once. The standard gas may be measured before and after the sample or after a series of sample measurements. While continuous-flow IRMS instruments can achieve higher sample throughput and are more convenient to use than dual inlet instruments, the yielded data is of approximately 10-fold lower precision. Such devices and methods are well known to those of skill in the art (see, e.g., U.S. Pat. No. 6,486,474, incorporated herein by reference).

SUMMARY OF THE INVENTION

The invention provides devices including a chamber appropriately sized to enclose a subject. The chamber includes a rigid enclosure and a rigid lid for the enclosure wherein when the lid is secured on the enclosure, an airtight seal is formed between the lid and the enclosure. The chamber and the lid enclose a space of defined volume that can be adjusted by use of spacers. In an embodiment, the invention provides a gasket for the formation of the airtight seal between the lid and the enclosure. Such an embodiment can include a latch for securing the lid to the enclosure. In an embodiment, the lid can be a screw-top or include other structures such as hooks, slots to secure the lid on the enclosure to form an airtight seal. The device further includes at least one port for airtight attachment of a syringe, and at least one port for airtight insertion of a gas sensor. In an embodiment, the device includes a second port for attachment of a second syringe. In an embodiment, the device includes a second port for attachment of a second gas sensor.

The invention provides for devices that include one or more syringes attached to the chamber, preferably each syringe is attached to the device through a three-way stopcock attached to a syringe port wherein the attachments provide airtight seals between the components. In an embodiment, the invention provides a device including a vacuum tube adapter operably linked to a port on a three-way stopcock.

The invention further provides for a device including one or more gas sensors wherein the gas sensor is inserted into the device through an airtight port. In an embodiment, the one or more gas sensors are operably linked to one or more detectors. The invention further includes a device of the invention enclosing a subject.

The invention further provides method of use of the devices of the invention for direct gas measurement for measuring the real-time metabolic product production of a study subject simultaneously with isotopic enrichment of exhaled gas. The method includes providing a device of the invention including a chamber wherein the chamber includes a rigid enclosure a rigid lid for the enclosure. The device preferably includes a gasket between the lid and the enclosure providing an airtight seal between the enclosure and the gasket upon closure of the lid, preferably with a latch. The device further includes a port operably linked to a three-way stopcock having three stopcock ports. The stopcock is operably linked to the chamber in a first stopcock port, and operably linked to a syringe in a second stopcock port. The chamber also includes a port for airtight insertion of a gas sensor with a gas sensor inserted into the port.

The method is performed by placing a subject contacted with a metabolic substrate containing an isotope in the chamber and closing the lid of the enclosure to provide an airtight chamber. The gas concentration is measured inside the airtight chamber using the gas sensor. A self-sealing vacuum tube is operably attached to the three-way stopcock at a third port.

The three-way stopcock positioned to connect the syringe to the chamber, but not outside air, and an air sample of defined quantity from the chamber is drawn into the syringe. The three-way stopcock positioned to connect the syringe containing the chamber air to the self-sealing vacuum tube, but not the chamber, and the chamber air is expelled from the syringe into the tube. The tube is removed from the adaptor, and a new tube is optionally placed into the adaptor if a subsequent sample is to be collected. A three-way stopcock is positioned to connect the syringe to outside air, but not to the chamber. A volume of outside air having the same volume as the chamber air sample is collected in the syringe. Outside air can include any air that is not in the chamber, including ambient air or air from another source. The three-way stopcock is positioned to connect the syringe containing the outside air to the chamber, but not the outside air, to expel the defined quantity of outside air in the syringe into the chamber. The method can be repeated to collect samples at multiple time points. The isotope in the metabolic product in the sample collected in the vacuum tube is detected, for example by using IRMS. The amount of the metabolic product containing the isotope is compared to the total amount of the same gas present in the chamber and detected by the gas sensor.

DEFINITIONS

As used herein, "airtight" as in airtight connection, airtight seal, or airtight chamber is understood as a point for insertion or attachment of a component of the device to the chamber, or the chamber itself, such that air does not unintentionally enter or leave the chamber or enclosed portion of the device through the insertion or attachment point of a device, or between the lid and the walled enclosure. A stopcock can intentionally be opened to allow air to flow into the syringe, or outside air can be provided into the chamber from a syringe in the context of an airtight container. For example, a syringe, optionally with a stopcock, can be attached to a chamber by an airtight connector to the chamber using a Luer lock connector, bayonet connector, rapid release connector, quick connector, screw connector, compression connector. The gas detector can be inserted through an opening that includes a gasket so that an airtight seal is formed upon insertion of the gas sensor into the port in the chamber. A gasket can be inserted between, or be a component of the lid or the enclosure portion of the chamber to allow for an airtight seal between the lid and the walled enclosure.

"Analyte" is understood as any compound that may be present in a sample that can be detected using an assay or method, for example by IRMS.

As used herein, "appropriately sized" for example as in relation to the device is understood as the device being sufficiently large to comfortably hold the subject and any barriers to prevent contact by the subject with the sensors and ports as needed for the duration of the experiment when all of the probes and other devices are inserted (e.g., $CO_2$ sensor, $O_2$ sensor). The appropriate size for the device will also depend on the rate of metabolism of the substrate especially when the size of the device and the subject is relatively small (e.g., mouse, rat, flies, cells in culture) or the $CO_2$ production rate is high, from the test subject or substrate to be studied. For example, a substrate that it metabolized quickly will preferably be detected in a somewhat larger chamber to decrease the rate of accumulation of a metabolite, whereas a more slowly metabolized substrate may benefit from being assayed in a smaller device if the threshold of detection is reached sooner. Because this device and method affords real-time monitoring of $CO_2$ production by the test subject, adjustments of device size and study time can be adjusted as needed to produce desired time and expired $CO_2$ production to allow optimal enrichment for IRMS analysis. The device should also be appropriately sized such that the decrease in the oxygen level in the device during the time of the study is not hazardous to the subject and that $CO_2$ generated by the test subject achieves an optimal level to allow IRMS detection of enrichment, without narcotization of the subject. It is understood that the size of the device can be sized by changing the size of the device at the time of manufacture, or by the insertion of spacers into the device to displace air at the time of use. In an embodiment, the positions of the walls of the chamber are adjustable.

"Contacting" as used herein is understood as administering (e.g., enterally, parenterally, by inhalation, etc) or addition to growth media in such a way that the substrate is delivered to a cell to be tested for metabolism of the substrate.

As used herein, "detecting", "detection" and the like are understood as an assay or method performed for identification and/or quantitation of a specific analyte in a sample. The amount of analyte detected in the sample can be none (zero) or below the limit of detection (<LOD), positive and within the calibrated range, or positive and outside of the calibrated range of the assay or method.

A "gas sensor" as used herein is understood as a device that can provide a reading in real time of the concentration of gas in contact with the sensor (e.g., gas in a chamber, ambient air) in percent, parts per million, or any other standard unit. A gas sensor for use in the methods and devices of the invention include $CO_2$ sensors, $O_2$ sensors, $N_2$ sensors, $H_2$ sensors, $NH_3$ sensors, CO sensors, $N_2O$ sensors, and $H_2S$ sensors. Such sensors are available from a number of commercial sources. The specific detector is not a limitation of the invention, however in a preferred embodiment, laser diode probes are used. A sensor is typically attached to a detector that provides a display and/or a recording device to allow for tracking of the gas concentration detected by the sensor. The specific properties of the detector are not a limitation of the invention. In an embodiment, the detector can be integrated into the gas sensor as a single device.

A "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoroethylene). It is usually desirable that the gasket be made from a material that is to some degree yielding such that it is able to deform and tightly fills the space it is designed for, including any slight irregularities. Gaskets can require an application of sealant directly to the gasket surface to function properly.

As used herein, "kits" are understood to contain two or more components of the device of the invention, or components for use with a device of the invention, in appropriate packaging or with instructions for use.

As used herein, "latch" is understood as any type of structure that can be used to hold the lid tightly on the enclosure to provide an airtight seal. For example a latch can be one or more of any of various devices in which mating mechanical parts engage to fasten something such as a pivoted bar that falls into a notch, a spring slides a bolt into a hole, wherein the closure device can be closed sufficiently tightly to form an airtight seal. A latch can also include one or more notches in the lid that mate with one or more notches in the enclosure to provide an airtight seal, e.g., a screwcap. In an embodiment, the latch can include the use of Velcro® or other fabric closures consisting of a piece of fabric of small hooks that sticks to a corresponding fabric of small loops. A latch can include an elastic or other material that is stretched around the device.

"Methylmalonic academia" (MMA), also called "methylmalonic aciduria," is an autosomal recessive metabolic disorder. It is a classical type of organic acidemia. Methylmalonic acidemia stems from several enzymatic subtypes and genotypes, severe forms of the disorder are usually diagnosed in the early neonatal period, and present with progressive encephalopathy, and, in some cases, secondary hyperammonemia. The disorder can result in death if undiagnosed or left untreated. The inherited forms of methylmalonic acidemia are caused by defects in the metabolic pathway where methylmalonyl-coenzyme A (CoA) is converted into succinyl-CoA by the enzyme methylmalonyl-CoA mutase. An activated form of vitamin B12, 5'-deoxyadenosylcobalamin, is also needed for the conversion of methylmalonyl-CoA to succinyl-CoA. Mutations leading to defects in vitamin B12 metabolism or in its transport frequently result in the development of methylmalonic acidemia, and in some cases, hyperhomocysteinemia, and can have a similar neonatal metabolic phenotype. Methylmalonic acidemia has varying diagnoses, treatment requirements and prognoses, which are determined by the specific genetic mutation causing the inherited form of the disorder.

"Obtaining" is understood herein as manufacturing, purchasing, or otherwise coming into possession of.

"Operably linked" or "operably joined" are understood as a connection, either physical or electronic, between two components of the device, e.g., between a gas sensor and a detector, between a chamber, a stopcock, and a syringe.

As used herein, "plurality" is understood to mean more than one. For example, a plurality refers to at least two, three, four, five, ten, 25, 50, 75, 100, or more.

"Port" as used herein is understood as a feature for operable connection, preferably airtight connection, of two components of the device. A port typically includes an opening to allow for operable connection between two components of the device.

A "sample" or as used herein is understood as a quantity of air obtained from a chamber of the invention during an experiment (either a control sample or a test sample), or a control sample containing ambient air, or air containing a known quantity of an isotope of interest.

A "subject" as used herein refers to a living cell or organism. In certain embodiments, the living organism is an animal, such as an insect (e.g., *drosophila*) or a worm (*C. elegans*). In certain embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient. A "subject" as used herein can also be understood as cells in culture, for example, primary or immortalized cells in culture, including cells from a normal subject or a subject including a disease or disorder, particularly a metabolic disorder.

"Substrate", "metabolic substrate", and "tracer" as used herein is understood as a compound that can bind to an enzyme that catalyzes the production of a product. An "isotopically labeled substrate" is a substrate that includes at least one isotope not the predominant isotope in air such as $^2H$, $^{11}C$, $^{13}C$, $^{15}N$, or $^{18}O$, which are referred to as "heavy atoms" incorporated into the substrate for administration. An isotopically labeled substrate will typically be present at a known concentration in a mixture with the same substrate which is not isotopically labeled. The concentration of isotope present can be known as the specific activity of the mixture.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

Any devices or methods provided herein can be combined with one or more of any of the other devices and methods provided herein.

BRIEF DESCRIPTION OF THE FIGURES

FIG. 4 shows the results of an assay using a device and method of the invention to determine $^{13}C$ propionyl-CoA metabolism in treated and untreated MMA mice one year after neonatal AAV gene therapy. 1-$^{13}C$-propionate oxidation. 200 micrograms of 1-$^{13}C$-sodium propionate was injected IP into Mut$^{+/-}$ (♦) (n=8), 1×10$^{11}$ GC AAV8-mMut treated Mut$^{-/-}$ (■) (n=3) or untreated Mut$^{-/-}$ (▲) (n=6) mice. $^{13}C$ enrichment in expired $CO_2$ was measured and used to determine the percent of the administered 1-$^{13}C$-propionate dose that was oxidized. Error bars surround the ninety five percent confidence intervals. The AAV8-mMut treated mutant mice show a significant increase in the ability to oxidize 1-$^{13}C$-propionate compared to the untreated Mut$^{-/-}$ mice at 25 minutes (p=3.9×10$^{-3}$). p-values were calculated using a Kruskal-Wallis test.

DETAILED DESCRIPTION AND PREFERRED EMBODIMENTS

The invention provides a respiratory chamber and method preferably using isotope ratio mass spectrometry, for direct gas measurement, such as $CO_2$ measurement, to measure in vivo oxidation rates of amino acid substrates, organic acid substrates, carbohydrate substrates, and fatty acid substrates in subjects by the detection and quantitation of $^{13}CO_2$ production. The devices and methods provided herein are useful to study in vivo intermediary metabolism in subjects and are useful to measure the effect of various therapeutic interventions, such as gene and cell therapy in patients who suffer from a variety of metabolic disorders. The devices and methods can be used to study the production of essentially any exhaled gas that is produced by a subject, either a normal subject or a subject having a disease or disorder, especially a metabolic disease or disorder, such gases can include $CO_2$, $O_2$, $N_2$, $H_2$, $NH_3$, CO, $N_2O$, and $H_2S$.

A proof of principle study demonstrating the use of the device is provided herein. Mice suffering from the metabolic disorder methylmalonic acidemia (MMA) were demonstrated to produce a significantly reduced amount of $^{13}CO_2$ after administration of 1-$^{13}C$ propionic acid as compared to wild-type animals. After administration of an adeno-associated viral vector (AAV) containing the coding sequence for the methylmalonyl-CA mutase gene which was deleted in the knockout mice, the pathway activity was restored as demonstrated by production of $^{13}CO_2$ at a rate comparable to an unaffected control littermate mouse after administration of the substrate.

The devices and methods provided herein allow for the analysis of intermediary metabolism by simultaneously measuring the production rate of both labeled and unlabeled metabolite, such as $CO_2$, in a subject administered an isotopically labeled substrate. The substrate can be administered by any route of administration, for example by injection or gavage. Substrates for use in the invention include organic acids, such as propionate, lactate, acetate, bicarbonate, and pyruvate; amino acids, such leucine, tyrosine, glycine, phenylalanine, valine, methionine, lysine, tryptophan, cysteine, serine, alanine, citrulline, glutamine, or ornithine; keto acids, such as alpha-ketoisocaproic acid; fatty acids, such as octanoate, palmitate, butyrate, hexanoate, or stearate; cholesterol and bile acids; such as cholesterol, chenodeoxylcholic acid, or deoxy chenodeoxylcholic acid; or simple carbohydrates, such as glucose, galactose, or fructose. The substrate contains one or more atoms that are labeled with a heavy non-radioactive atom. Metabolism converts the precursor into a metabolic product which is exhaled, a small fraction of which contain the heavy atom from the administered metabolic precursor or tracer.

Depending on the metabolic precursor administered, and the gas detected, the device and method can be used to study amino and organic acid oxidation in subjects with organic acidemias such as methylmalonic, propionic and isovaleric acidemia, amino acid oxidation in subjects with aminoacid disorders such as maple syrup urine disease and phenylketonuria, ureagenesis in subjects with urea cycle disorders; sulfite metabolism in subjects with defective ability to produce and/or oxidize sulfur containing amino acids; ketosis, gluconeogenesis, and glycolysis can be studied in subjects having impaired carbohydrate or fatty acid oxidation defects or have reduced ability to form ketones from fatty acids.

The expired air is collected using a respiratory chamber of the invention that allows the total carbon dioxide emitted by the animal in the chamber to be determined using a closed system. At timed intervals, small aliquots of the chamber gas are removed and placed into self-sealing vacuum tubes. The enrichment of heavy atom containing metabolic products, such as carbon-13 containing $CO_2$, in these samples is separately measured from the total specific gas of interest produced, such as carbon dioxide, in the air in the chamber which is measured in real time as the samples for detection of heavy atom metabolic products, for example by IRMS, are collected. Using the two measurements, the amount of metabolized substrate can be uniquely determined. Because the compounds used as metabolic substrates derive from substances whose general metabolic steps are known, the activity of pathways and entire processes can be measured. Furthermore, as the technique uses stable isotopes, treated animals can be returned to the cage after study with no concerns of radioactive contamination as the heavy atoms are not radioactive.

The devices and methods provided herein can be used to determine or monitor the activity of therapeutic interventions such as genes, cells, small molecules, and enzyme replacements that are delivered to subjects that are decreased, absent, or non-functional enzymes in the pathway(s) under study, as a way to measure the efficacy of the therapeutic interventions being tested. As demonstrated herein, the technique to demonstrate restoration of the propionate oxidation pathway in a mouse model of methylmalonic academia, a common organic anemia, after gene therapy. The method can be extended to numerous other metabolic diseases, such as phenylketonuria, maple syrup urine disease, tyrosinemia, alkaptonuria, hyperhomocysteinemia, cystinosis; numerous fatty acid oxidation defects, such as very long, medium, short and multiple acyl-CoA dehydrogenase deficiency, long chain hydroxylacyl-CoA dehydrogenase deficiency, carnitine transporter defect, and ketone body synthetic disorders; glycolytic defects, and a large group of organic acid metabolic disorders, including methylmalonic acidemia, propionic acidemia, glutaric acidemia, isovaleric acidemia, 3-methylcrotonylCoA decarboxylase deficiency, and urea cycle disorders, such as citrullinemia. These metabolic diseases have been characterized as a deficiency to metabolize one or more specific substrates. The method can be used to study small animals such as mice as well as patients who might receive gene or cell based therapies or enzyme replacement therapy as a treatment for their underlying disorder.

Figure 1A:
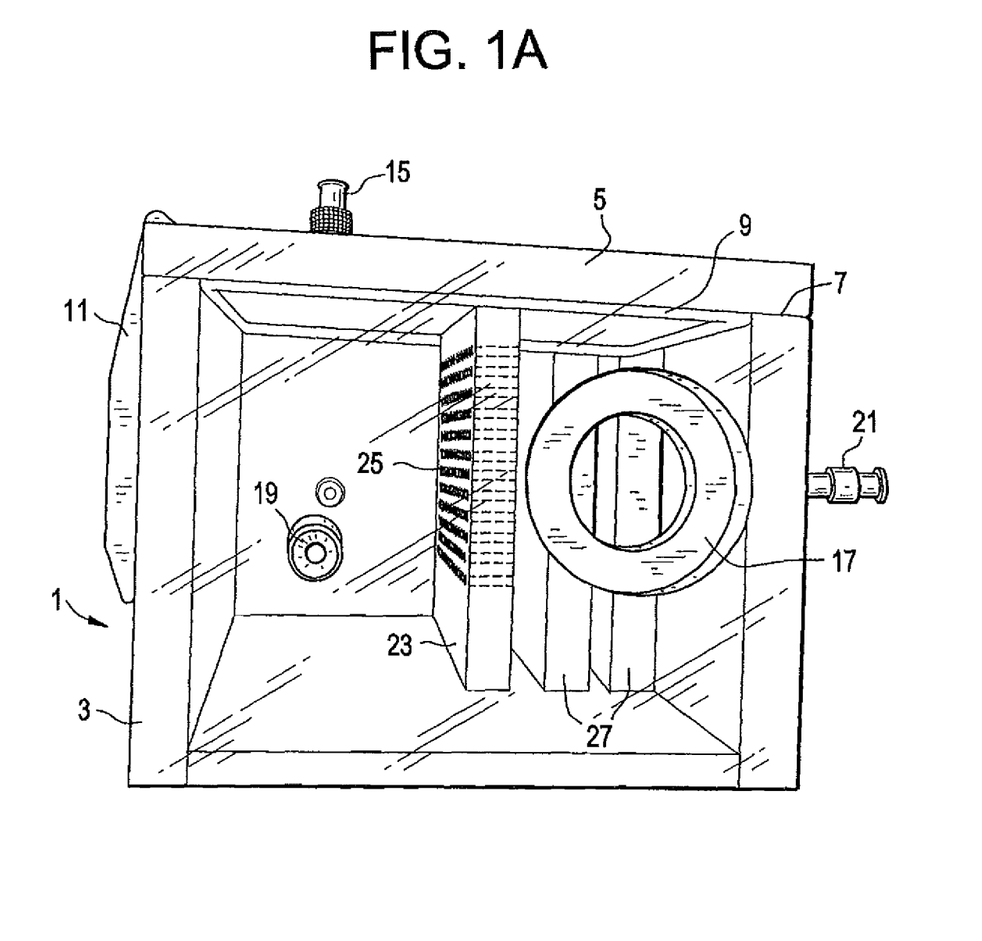
FIGS. 1A and 1B show A) a side view, and B) a top view of an embodiment of the chamber.
Figure 1B:
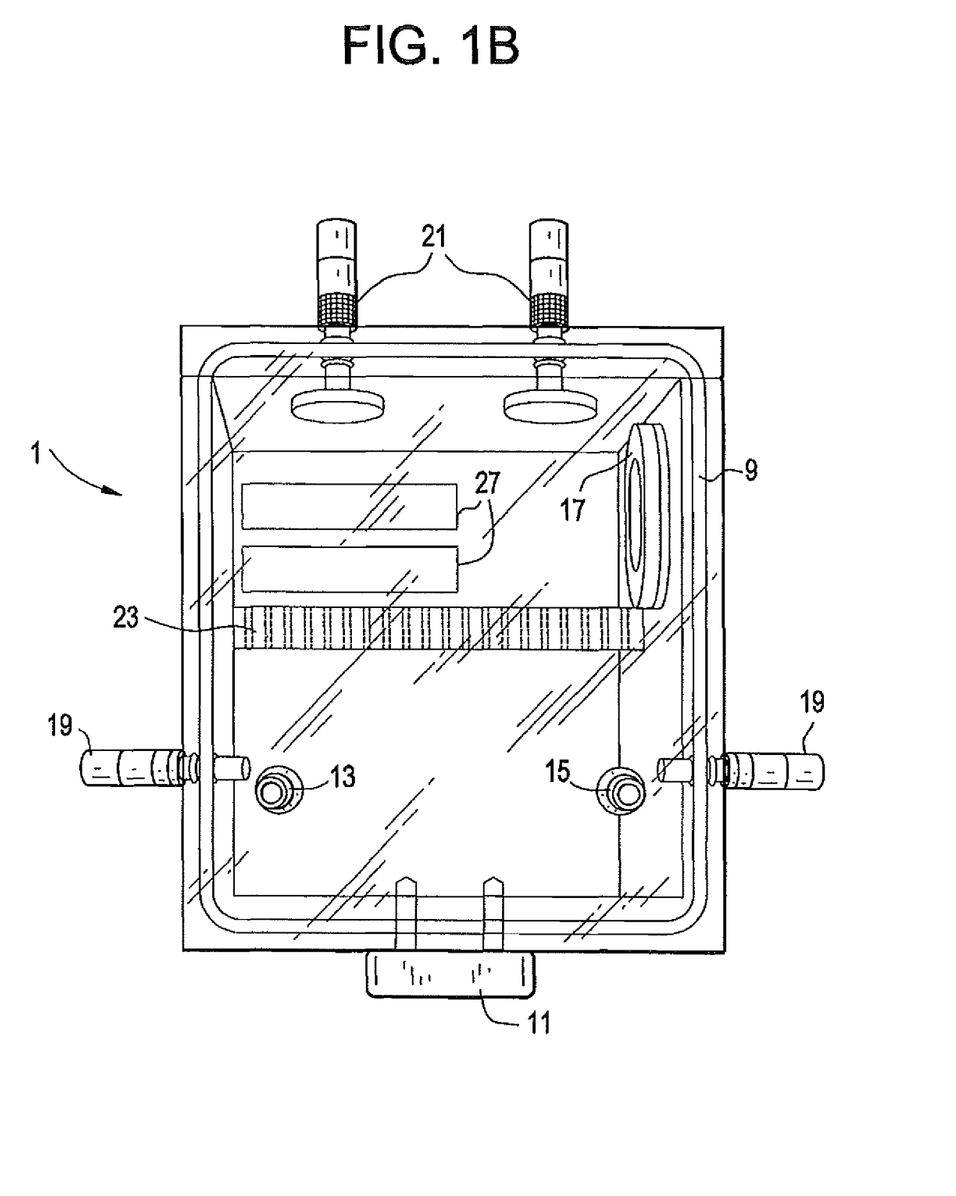
Figure 2A:
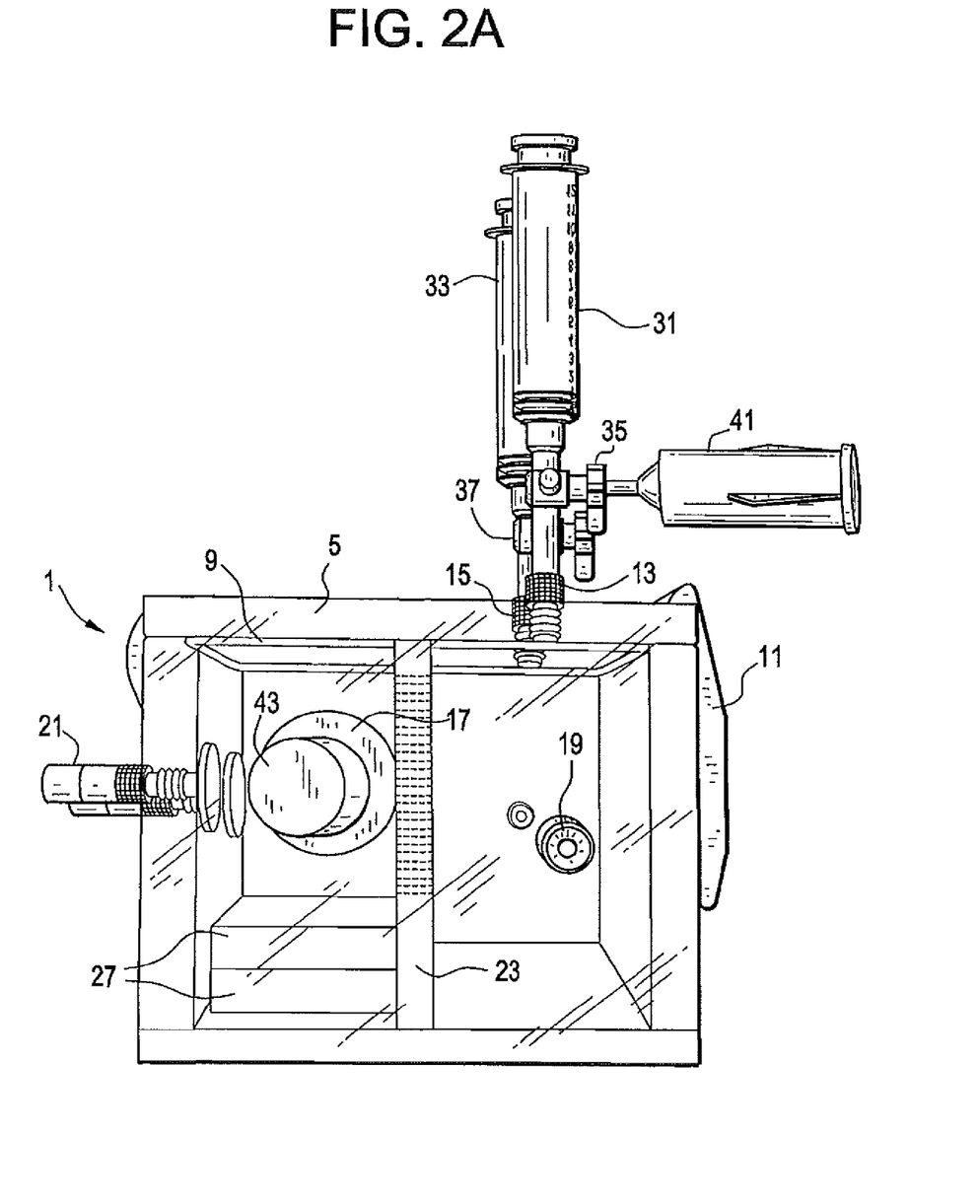
FIGS. 2A and 2B show A) a first side view, and B) a second side view of an embodiment of the chamber.
Figure 2B:
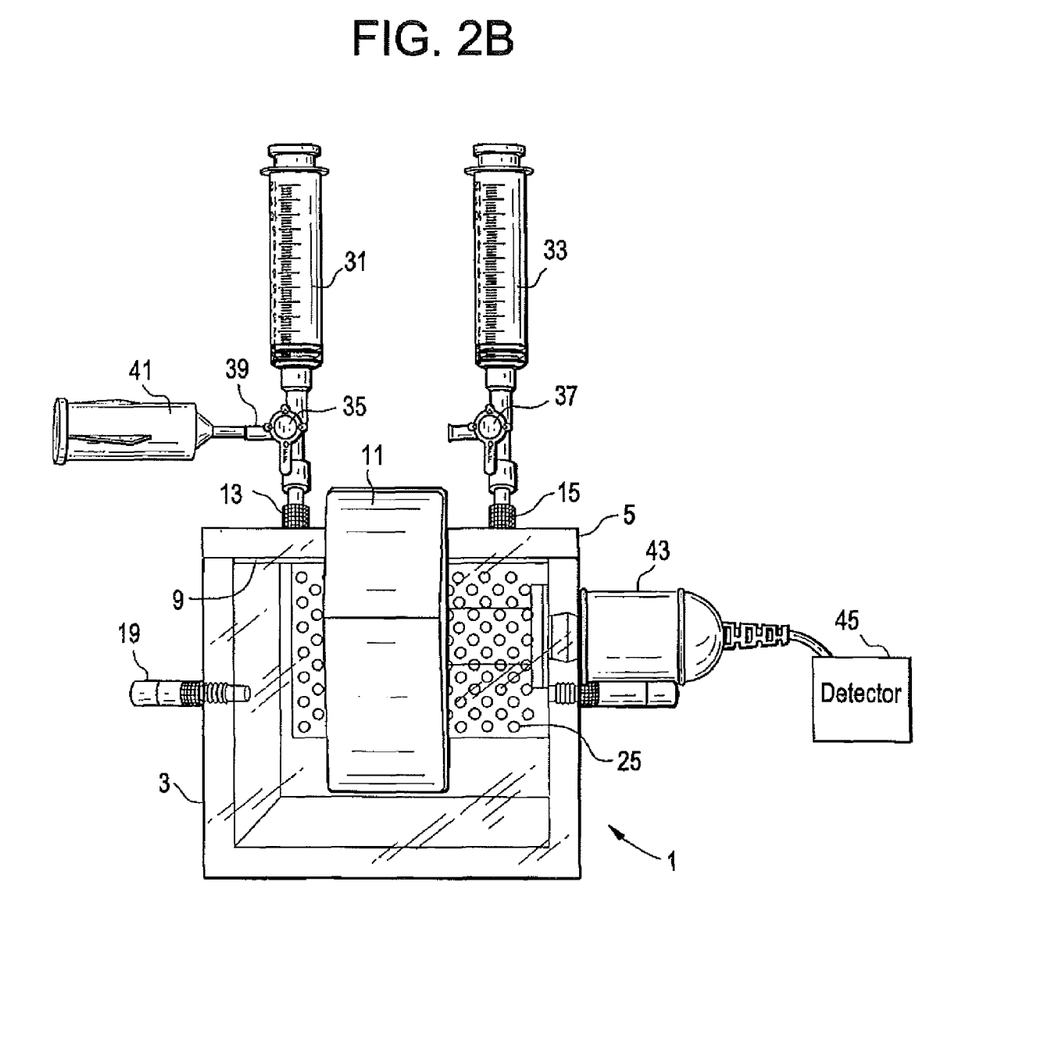

Embodiments of the device are shown in the figures. FIGS. 1A and 1B show an embodiment of the chamber of the device without any removable/interchangeable components present. The chamber 1 includes a walled portion of the enclosure 3 for placement of the subject. The chamber preferably includes at least one side, other than the bottom, that is clear, to allow for observation of the subject in the chamber. The chamber is made of a rigid material to maintain a constant volume of the chamber. Preferably the entire enclosure and lid are made of substantially clear, essentially unbreakable material (e.g., plexiglass, clear plastic such as polycarbonate) that can be subject to common laboratory detergents and sterilization by heat and/or gas. A hinged lid 5 is attached to a top edge 7 of the walled portion of the enclosure. A gasket 9 between the walled portion of the enclosure and the lid, preferably attached to either the walled portion of the enclosure 3 or the lid 5, creates an airtight seal between the two portions of the enclosure when the lid is closed with the latch 11 and the removable components are attached to the chamber (as shown in FIG. 2). In an alternative embodiment, the lid can be completely removable from the chamber and fastened to the chamber by at least two latches. In an alternative embodiment, the lid and top edge of the enclosure can be appropriately shaped such that cut-outs, hooks, loops, or other structures of the lid mate with corresponding cut-outs, hooks, loops, or other structures of the enclosure. In an alternative embodiment, the lid can be retained in place by a strap placed around the device. In an embodiment, the lid can be screwed onto the lid when the enclosure is round, or can be designed so that the lid fits tightly into the walled enclosure providing an airtight seal. Such variations are well understood by those of skill in the art. The chamber includes two ports 13 and 15 in the lid for attachment of syringes using airtight connectors, and a gasket lined port 17 for insertion of a gas sensor. In the embodiment shown, the chamber optionally includes additional ports 19 and 21 for injection of materials (e.g., gases, liquids) that can include gaskets for puncturing 19 or locking connectors for syringes or tubing 21. In the embodiment shown, the interior of the chamber includes a barrier 23 having perforations 25 to protect the gas sensor and the ports from the subject when a sufficiently large and mobile subject is placed in the chamber. The specific location of the ports for syringe attachment and insertion of the gas sensor are not limitations of the invention. In a preferred embodiment, the ports for syringe attachment and the port for insertion of the gas sensor are sufficiently close to each other to allow the ports to be partitioned off by the barrier if needed. The use of a barrier will depend on the subject to be placed in the device. For example, no barrier is required for use of the device with culture cells or *C. elegans*. Further, the size of the perforations 25 in the barrier will depend on the subject to be tested. For example, perforations for use of the device with drosophila may need to be smaller than those used with mice.

Such considerations are well understood by those of skill in the art. The device can further include spacers 27 for placing in the chamber to adjust the effective size of the chamber without the need to build a new chamber. The spacers are of a known volume which is subtracted from the volume of the chamber.

FIGS. 2A and 2B show the chamber 1 with syringes 31 and 33 attached by 3-way stopcocks 35 and 37 to the syringe ports 13 and 15 in the lid 5 of the enclosure. The second port 39 of the 3-way stopcock 35 is attached to a vacuum tube adapter 41. A self-sealing vacuum tube can be placed into the sleeve of the adapter and punctured with the needled inside the adapter to operably link the syringe to the self-sealing vacuum tube. A gas sensor 43, such as a $CO_2$ sensor, is inserted through a gasket lined port 17 in the side of the chamber 1 to create an airtight connection between the chamber and the sensor. The gas sensor is connected to a detector 45 device that displays and/or records the gas level within the chamber, either continuously or periodically. In an embodiment, the sensor can be integrated into the chamber wall and contain a wireless transmission circuit for remote monitoring.

Figure 3A:
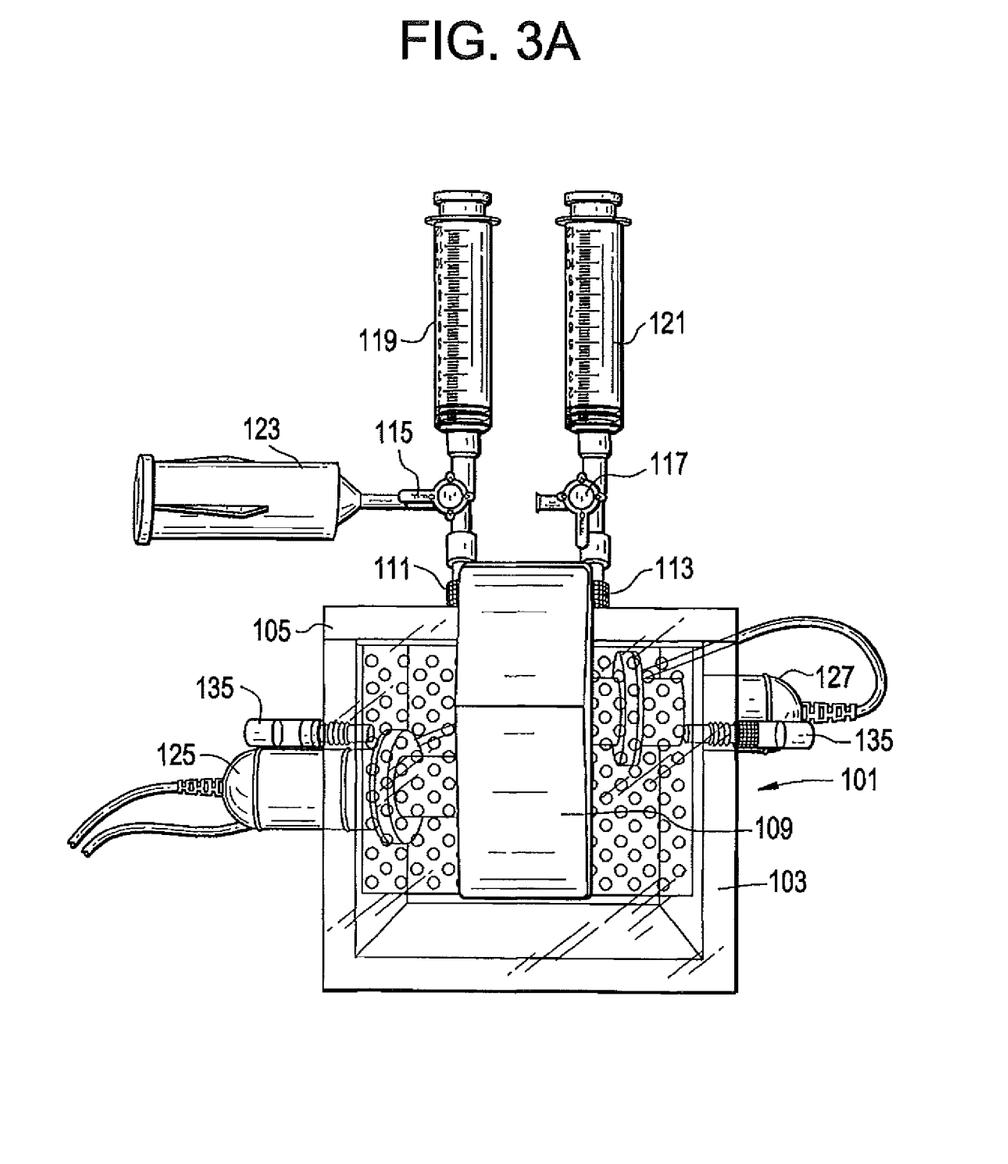
FIGS. 3A and 3B show A) a side view and B) a top view of an embodiment of the chamber with two ports for gas detectors.
Figure 3B:
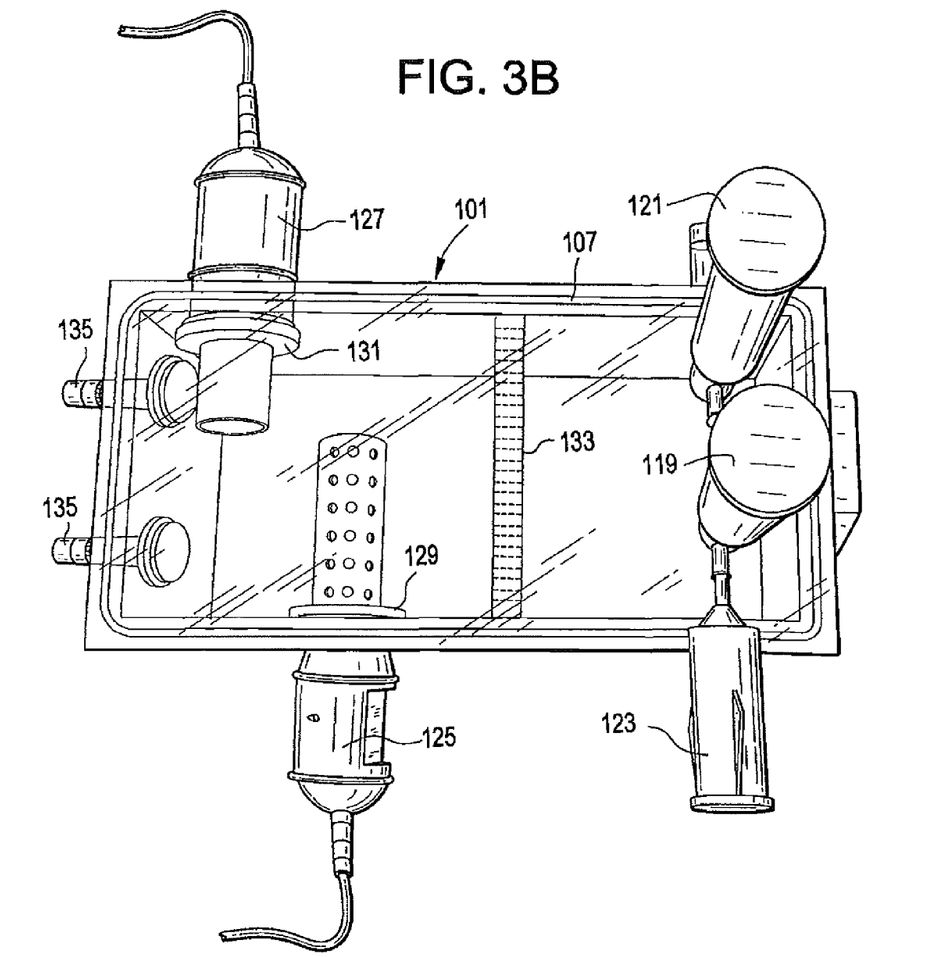

FIGS. 3A and 3B show a side view and a top view of an alternative embodiment of a device of the invention including two ports for insertion of one or two gas sensors, for example an $O_2$ sensor and a $CO_2$ sensor. The device can readily be used with a single sensor by inserting a rubber stopper or other similar device into the port not containing a gas sensor. As in FIGS. 1 and 2, the chamber 101 includes a walled enclosure 103 and a hinged lid 105. A gasket 107 between the walled enclosure and the lid provides an airtight seal upon closure of the latch 109 when the removable components are attached as shown. The lid includes two ports 111 and 113 for attachment of three-way stopcocks 115 and 117 which are further attached to syringes 119 and 121. A port of stopcock 115 is attached to a vacuum tube adaptor 123. First 125 and second 127 gas sensors are inserted through first 129 and second 131 gasket-lined ports in the chamber. The embodiment shown further includes a perforated barrier 133 and additional ports 135 for the introduction of gas or other material into the chamber. The use of a device with multiple ports for gas sensors is advantageous for monitoring the release of two gases. The use of a device with multiple ports for gas sensors is also advantageous when the gas to be detected is neither $O_2$ nor $CO_2$. The change in the concentration of either $O_2$ or $CO_2$ in the device is an indication that all of the seals in the device are airtight.

A method of use of the devices of the invention is readily described making reference to the figures. The method as described makes reference to the embodiment of the device in FIG. 2. However, the method can be practiced using any device of the invention.

A subject is inserted into the enclosure 3 and the lid 5 is closed. The $CO_2$ level and/or $O_2$ level in the chamber are monitored using the gas sensor 43 to insure that the chamber is sealed (e.g., $CO_2$ level increase, $O_2$ level decrease). The stopcocks 35 and 37 are positioned to prevent air exchange between the chamber and ambient air, i.e., the lever is pointed to the left in the embodiment shown. The air is completely expelled from the syringes 31 and 33 prior to closure of the lid. At the desired time interval, a predetermined volume of air is pulled from the chamber 1 into syringe 31. A self-sealing vacuum tube is placed into the vacuum tube adaptor 41 to operably link the tube to the adaptor. The stopcock 35 is rotated to prevent air exchange between the chamber and ambient air but to allow air exchange between the syringe and the self-sealing vacuum tube, i.e., the lever is pointed down in the embodiment shown. Air is completely expelled from the syringe 31 into the self-sealing vacuum tube in the vacuum tube adaptor 41. To maintain a constant volume of gas in the chamber throughout the course of the experiment, stopcock 37 is rotated to prevent ambient air from entering the chamber, but to allow ambient air to be drawn into the syringe, i.e., the lever is pointed down in the embodiment shown. The same volume of air that was withdrawn from the chamber and transferred into the self-sealing vacuum tube is pulled into syringe 33. The stopcock 37 is rotated to allow air to flow from the syringe to the chamber, but to prevent exchange with ambient air, i.e., the lever is pointed left in the embodiment shown. The air in the syringe 33 is expelled into the chamber 1. As the amount of heavy isotopes present in ambient air is negligible, therefore, no adjustments need to be made in relation to the content of the air. In an alternative embodiment, $O_2$ or $O_2$ enriched air can be provided to the device instead of ambient air one or more times during the method to prevent distress of the subject. The variation would be particularly useful in experiments of extended duration or in which a smaller enclosure was used. The steps of sample collection are repeated the desired number of times to collect the desired number of samples. The subject is observed to insure that the decrease in $O_2$ in the chamber or an increase in $CO_2$ in the chamber does not cause undue stress in the subject. When using cells, it may be preferable to warm the chamber to maintain the cells at or around 37° C. With certain types of tissue culture cells, it may also be beneficial to provide the cells with additional $CO_2$, for example through one of the ports not attached to a syringe.

After collection of control data, and preferably a recovery period, the subject is administered or contacted with an isotopically labeled substrate by injection, gavage, orally, intravenous infusion or other method of administration, or by incorporation into growth media or food, and the same steps for sample collection are performed. In a preferred embodiment, collection of a first sample in the self-sealing vacuum tube is performed as soon as possible after contacting the subject with the isotopically labeled substrate.

It is understood that the device can include a single port for attachment of a syringe coupled to a three-way stopcock. However, such a set-up requires the removal of the vacuum tube adapter to allow ambient air to be pulled into the syringe. Such considerations would be well understood by those of skill in the art.

The method of the invention can be practiced without the reintroduction of air into the chamber after sample collection. However, replacement of the removed air allows for calculations to be made based on a constant gas volume. Additionally, because the replaced ambient air has a minimal and known concentration of heavy atoms, for example carbon dioxide, equal to 362 parts per million or less than 0.03% in most locations and negligible amounts of carbon 13 carbon dioxide, effects on the carbon dioxide production rate measurement of the test subject are insignificant but can be accounted for precisely because the method uses a constant volume. Moreover, it eliminates a potential source of undue stress for the subject (e.g., reduced air pressure, hypoxia) and can allow "pure" oxygen to be administered is an isovolemic fashion if needed.

Samples collected in self-sealing vacuum tubes are assayed to determine the amount of isotopically labeled product is present using any method, such as IRMS. The ratio of labeled to unlabeled product is determined for both control and test samples.

The device and method of the invention can be scaled for use with subjects of varying size (e.g., mouse, human, subjects grown in culture). The larger the size of the subject relative to the device, the more carefully the volume of the subject must be considered in calculations. Such considerations are well understood by those of skill in the art.

The embodiments shown include syringe ports in a flat lid on the top of the chamber. It is understood that the chamber as created by the walled enclosure and the lid as shown in the drawings can be an assembly of any container that provides an opening sufficiently large for the subject to be placed into and removed from the chamber that can be closed to generate and airtight seal. Further it is understood that placement of the syringes on surfaces other than the lid of the device as shown in the figures will change the relative orientation of the stopcocks (i.e., if the orientation of the syringe is rotated 90 degrees, the position of the closed lever on the stopcock will necessarily need to be rotated 90 degrees from the position noted in conjunction with the drawings of FIG. 2, but be in the same position relative to the stopcock.

EXAMPLE

Methods
Administration of Adeno-Associated Viral (AAV) Vector Encoding Methylmalonyl-CoA Mutase for the treatment of Methylmalonic Acidemia (MMA)

A knockout mouse has been generated that includes a targeted deletion in the methylmalonyl-CoA mutase gene resulting in MMA in the mouse (Chandler et al., (2007) Metabolic phenotype of methylmalonic acidemia in mice and humans: the role of skeletal muscle, *BMC Medical Genetics* 8:64; Chandler et al., (2008) Mitochondrial dysfunction in mut methylmalonic acidemia. *FASEB J.* Dec. 16. [Epub ahead of print], both incorporated herein by reference). Homozygous knockout mice show symptoms of the disease in the first few days of life in one model and variably in another that uses a hybrid background and are typically viable for only several days after birth. An adeno-associated viral (AAV) vector encoding the methylmalonyl-CoA mutase protein was administered to the mice in the neonatal period. After several days, mice showed no physiological signs or symptoms of MMA. Mice were viable for at least a year without further treatment.

In an extension of the above approach, two rare MMA mutant survivor mice that lived until day of life (DOL) 20 were studied. The animals were runted, hypoactive and had massive levels of methylmalonic acid present in the blood and urine. They were studied to determine propionate oxidative capacity and given the AAV vector gene therapy. 10 days later, clinical appearance improved and propionate oxidation achieved the same level seen in a control littermate, even though the plasma metabolites were increased, showing that this method can be used to monitor gene delivery in the short and long-term setting.

Collection of $CO_2$ Samples From Mice Before and After Administration of $1$-$^{13}$C-Proprionate The barrier and spacers were placed in a chamber like the chamber shown in FIG. 2. Two syringes were attached to three-way stopcocks that were in turn attached to the lid of the chamber. An adapter for vacuum tubes was attached to the stopcock attached to the first syringe. A laser diode $CO_2$ probe was inserted into a port on the side of the chamber. All connections were airtight. All stopcocks were positioned to prevent ambient air from entering the chamber. The $CO_2$ probe was attached to the detector and a basal $CO_2$ level reading was taken. Total $CO_2$ in the chamber was monitored in real time throughout the course of the experiment. A mouse was placed in the chamber on the opposite side of the barrier from the $CO_2$ probe. The lid was closed and latched, and the $CO_2$ level was monitored. An increase in $CO_2$ in the chamber was observed demonstrating that the chamber was airtight.

A timer was started and at five minute intervals, samples of $CO_2$ were collected and the air in the chamber was replaced with ambient air by the following method. The stopcock on the first syringe was oriented to allow air to pass from the chamber into the syringe with no exchange with ambient air. A volume of 10 ml of air was withdrawn from the chamber into the syringe. A self-sealing vacuum tube was inserted into the vacuum tube adapter attached to the stopcock on the first syringe. The stopcock was rotated to permit airflow from the syringe into the self-sealing vacuum tube with no exchange with the chamber. The air was expelled from the syringe into the self-sealing vacuum tube, and the self-sealing vacuum tube was subsequently removed. The stopcock on the second syringe was rotated to permit ambient air to flow into the syringe with no air exchange with the chamber. A volume of 10 ml of ambient air was drawn into the syringe. The stopcock was rotated to permit air to flow from the syringe into the chamber without exchange with ambient air. The 10 ml of ambient air was expelled into the chamber.

The steps of sample collection and replacement of air volume with ambient air was repeated five more times to collect basal $CO_2$ release for the mouse. This series of control measurements was performed for each mouse as the $CO_2$ production rate was found to vary significantly between animals.

After completion of the control measurements, the mouse was allowed to rest in the chamber for about 5 minutes in open air to recover. The mouse was then injected intraperitoneally with 2 millimoles of 1-$^{13}$C-sodium propionate, using an adaptation of a method developed to study propionate oxidation in patients with methylmalonic and propionic acidemia. Upon closing the chamber, a timer was started, and samples were obtained at five-minute intervals using the same method as that used to collect the control samples prior to injection.

After sample collection was complete, the isotope ratio ($^{13}$C/$^{12}$C) of the expired gas was determined with a gas isotope ratio mass spectrometer. The percent dose metabolized at each time point was calculated as: % dose metabolized=Total $^{13}$C excreted (mmol/dose (mmol)× 100%). The same sample collection methods were used for all mice.

Results

Figure 4:
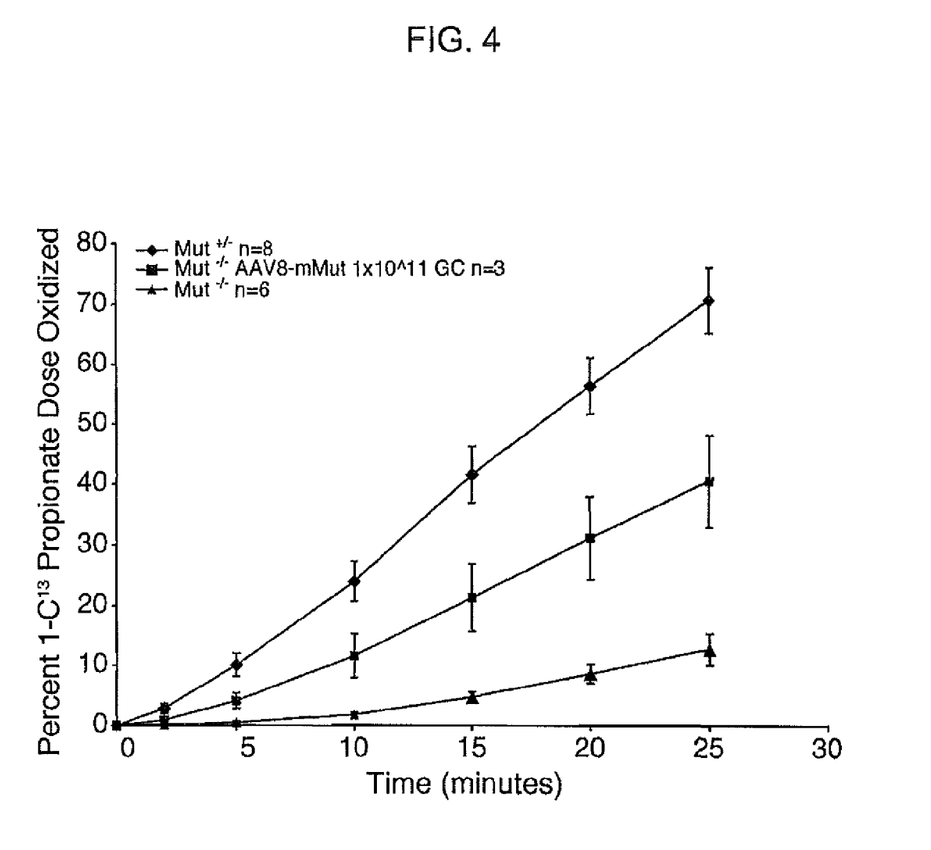

To examine whether the impressive long-term survival and ameliorated metabolite levels observed in the treated mutants corresponded with increased mutase enzymatic activity, whole animal in vivo propionate oxidation was measured. After determining the appropriate tracer dose to administer and examining the kinetics of 1-$^{13}$C-sodium propionate metabolism in control mice, animals were injected with 1-$^{13}$C-sodium propionate and the subsequent metabolism of this tracer through the methylmalonyl-CoA mutase reaction, into the Krebs cycle, with eventual oxidation into $^{13}CO_2$ was measured. As can be seen in FIG. 4, there is a vast discrepancy between the ability of the untreated mutants and heterozygous controls to convert the injected label into $^{13}CO_2$. Mut$^{+/-}$ heterozygotes metabolize approximately 80% of the uninjected dose in 25 minutes, while untreated mutants convert less than 15% of the dose, with very flat enrichment kinetics (not presented). At one year of age, the treated mutants show a marked increase in 1-$^{13}$C-sodium propionate metabolism and on average, can convert ~50% of the injected dose into $^{13}CO_2$ less than untreated controls but significantly increased compared to the untreated mutants (p=3.9×10$^{-3}$).

Figure 5:
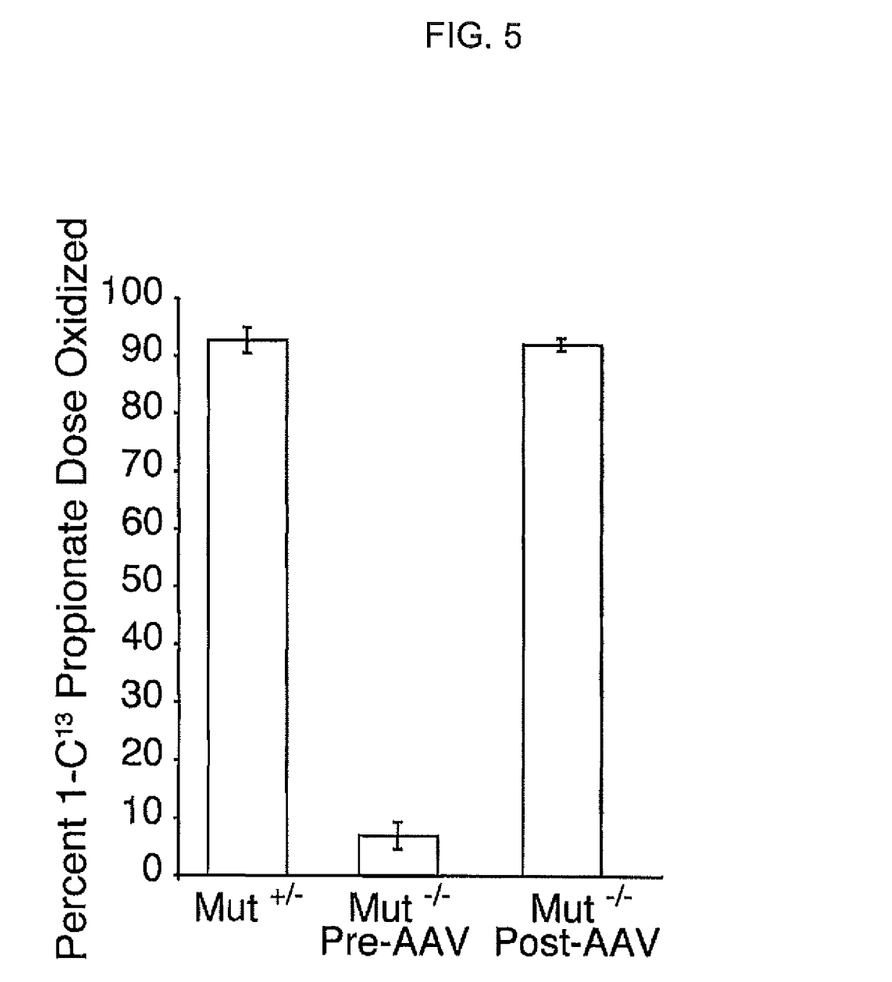
FIG. 5 shows the results of an assay using a device and method of the invention to determine $^{13}C$ propionyl-CoA metabolism in untreated (labeled Mut$^{-/-}$ AAV PRE) and treated (labeled Mut$^{-/-}$ AAV POST) MMA mice 10 days after receiving AAV gene therapy on day of life 20 compared to controls littermates (labeled Mut$^{+/-}$).

As an extension of using this technique and device to monitor the effects of AAV gene therapy beyond the immediate neonatal period, two rare untreated Mut$^{-/-}$ mice that survived until DOL 20 received a single intraperitoneal injection of 3×10$^{11}$ GC of rAAV8-mMut. At the time of injection, the animals were runted, hypoactive and showed an impaired ability to produce $^{13}CO2$ from 1-$^{13}$C— propionate. When studied 10 days after receiving the rAAV8-mMut, the animals had improved clinical appearance, rapid weight gain, lower circulating metabolites and had fully restored propionate oxidation, to the level seen in the untreated, age and diet matched heterozygous littermates (FIG. 5).

Those skilled in the art will recognize, or be able to ascertain using no more than routine experimentation, many equivalents to the specific embodiments of the invention described herein. Such equivalents are intended to be encompassed by the following claims.

All references, patents, and patent publications cited herein are incorporated herein by reference.

I claim:

1. A method for direct gas measurement for measuring isotope ratio comprising:
   a) providing a device comprising:
      1) a chamber wherein the chamber comprises:
      2) a rigid enclosure;
      3) a rigid lid for the enclosure wherein upon closure the lid and the enclosure form an airtight seal;
      4) a port operably linked to a three-way stopcock wherein the stopcock is operably linked to the chamber in a first stopcock port and operably linked to a syringe in a second stopcock port,
      5) at least one sensor port for airtight insertion of at least one gas sensor; and
      6) at least one gas sensor for insertion into the at least one port;
   b) placing a subject contacted with an isotope in the chamber;
   c) closing the lid of the enclosure to provide an airtight chamber;
   d) measuring a gas concentration inside the airtight chamber;
   e) operably linking a self-sealing vacuum tube to the three-way stopcock at a third stopcock port;
   f) providing the three-way stopcock positioned to connect the syringe to the chamber but not outside air;
   g) withdrawing an air sample of defined quantity of air from the chamber;
   h) providing a three-way stopcock positioned to connect the syringe to the self-sealing vacuum tube but not the chamber;
   i) expelling the air from the syringe into the tube;
   j) removing the self-sealing vacuum tube from the adaptor;
   k) providing a three-way stopcock positioned to connect the syringe to outside air but not to the chamber;
   l) collecting a volume of outside air having the same volume as the air sample;
   m) providing a three-way stopcock positioned to connect the syringe to the chamber but not the outside air;
   n) expelling the outside air into the chamber, and
   o) detecting the isotope in a gas in the sample from step (g).

2. The method of claim 1, wherein the gas detected with the gas sensor is the same as the gas in which the isotope is collected.

3. The method of claim 1, wherein the isotope is incorporated in a metabolic precursor.

4. The method of claim 1, wherein the gas detected with the at least one gas sensor is selected from the group consisting of $CO_2$, $O_2$, $N_2$, $H_2$, $NH_3$, $CO$, $N_2O$, $H_2S$ and combinations thereof.

5. The method of claim 1, wherein at least one gas detected with the at least one gas sensor is $CO_2$.

6. The method of claim 1, further comprising, prior to b) placing a subject contacted with an isotope in the chamber, positioning one or more spacers of defined volume within the chamber to adjust the effective size of the chamber.

\* \* \* \* \*